United States Patent
Unteregger (10) Patent No.: US 10,426,785 B2
(45) Date of Patent: Oct. 1, 2019

(54) C-19 STEROIDS FOR INHIBITING NEOVASCULARIZATION

(71) Applicant: Curadis GmbH, Erlangen (DE)

(72) Inventor: Gerhard Unteregger, Saarland (DE)

(73) Assignee: Curadis GmbH, Erlangen (DE)

( * ) Notice: Subject to any disclaimer, the term of this patent is extended or adjusted under 35 U.S.C. 154(b) by 0 days.

(21) Appl. No.: 15/535,461

(22) PCT Filed: Dec. 21, 2015

(86) PCT No.: PCT/EP2015/080762
§ 371 (c)(1),
(2) Date: Jun. 13, 2017

(87) PCT Pub. No.: WO2016/107778
PCT Pub. Date: Jul. 7, 2016

(65) Prior Publication Data
US 2017/0360804 A1    Dec. 21, 2017

(30) Foreign Application Priority Data
Dec. 30, 2014    (EP) .................................... 14200543

(51) Int. Cl.
*A61K 31/5685*    (2006.01)

(52) U.S. Cl.
CPC ...... *A61K 31/5685* (2013.01); *A61K 2300/00* (2013.01)

(58) Field of Classification Search
CPC ................................................ A61K 31/5685
See application file for complete search history.

(56) References Cited

FOREIGN PATENT DOCUMENTS

| EP | 1854465 A1 | 11/2007 | |
|---|---|---|---|
| EP | 2060300 | * 11/2007 | ............... A61K 9/10 |
| EP | 2060300 A1 | 5/2009 | |
| WO | 2007131736 A2 | 11/2007 | |
| WO | 2007131737 A2 | 11/2007 | |
| WO | 2009062683 A1 | 5/2009 | |

OTHER PUBLICATIONS

McMahon et al. (2000).*
Pinedo et al. (2000).*
Mukherji et al., Critical Reviews in Oncology/Hermatology 87 (2013), pp. 122-131.
Heidegger et al., J. Steroid Biochem. Mol. Biol., 138 (2013), pp. 248-256.
Franck-Lissbrant et al., Endocrinology, 139(2), (1998), pp. 451-456.
Liao et al., Mol. Biol. Rep., 40(12), (2013), pp. 6729-6735.
Traish and Galoosian, Korean J. Urol., 54, (2013), pp. 721-731.
Eisermann et al., Molecular Cancer 12(7), (2013), 13 pages.
Chao et al., Angiogeneris, 14(1), (2011), pp. 1-16.
Thomas et al., Fertil. Steril., 88(4 Suppl.), (2007), pp. 1065-1070.
D'Ascenzo et al., Toxicol. Lett., 169(2), (2007), pp. 129-136.
Galbiati et al., Pharmacol. Res., 65(2), (2012), pp. 221-230.
Paschoal et al., J. Sport. Med., 30(11), (2009), pp. 775-778 (Abstract).
Cao et al., ACS, 201(3 Suppl.), (2005), pp. 17-18, (Abstract).
Thorpe et al., Cancer Res., 53(13), (1993), pp. 3000-3007.
Bruemmer, Dennis, Arteriosclerosis, Thrombosis and Vascular Biology 32(2), (2012), pp. 161-162.
Cutolo et al., Arthritis and Rheumatism, 34(1), (1991), pp. 1-5.
Adam et al., H+G Zeitschrift fur Hautkrankheiten, 57(17), (1982), p. 1295.
European Search Opinion for application No. 14 200 543.9, dated Sep. 22, 2015.
International Search Report for PCT/EP2015/080762, dated Mar. 31, 2016.

* cited by examiner

*Primary Examiner* — Paul V Ward
(74) *Attorney, Agent, or Firm* — Seyfarth Shaw LLP (57) ABSTRACT

The present invention relates to the field of medicine, particularly to novel uses of C-19 steroid compounds having an androsten-17-($OR_4$)-3-one structure for inhibiting angiogenesis and particularly the proliferation and/or migration of endothelial cells in the treatment of diseases involving a pathological neovascularization and/or excessive regenerative processes.

13 Claims, 4 Drawing Sheets

C-19 STEROIDS FOR INHIBITING NEOVASCULARIZATION

FIELD OF THE INVENTION

The present invention relates to the field of medicine, particularly to novel uses of C-19 steroid compounds, more particularly to C-19 steroids having an androsten-3-one structure with specific structural configurations, in particular at the 4- and/or 17-position, for inhibition of neovascularization, angiogenesis and further uses. The present invention particularly relates to selected C-19 steroids inhibiting the proliferation and/or migration of endothelial cells and/or of smooth muscle cells in the treatment of diseases involving a pathological neovascularization and/or excessive regenerative processes being for instance associated with tumors or inflammatory conditions. Furthermore, the present invention relates to the reduction of the synthesis or expression, especially under therapeutic situations of inflammation and/or cancer and related conditions of associated tissues, of proliferation-, cancer- and/or inflammation-relevant growth factors or growth factor receptors, selected from the group consisting of vascular endothelial growth factor (VEGF), vascular endothelial growth factor receptor (VEGFR) and functionally related growth factors, notably fibroblast growth factor receptor 13 (FGFR 13), platelet derived growth factor receptor (PDGFR) a and/or ß, mast/stem cell growth factor receptor (SCFR; also known as c-Kit or tyrosine-protein kinase Kit or CD117).

DESCRIPTION OF THE BACKGROUND ART

Angiogenesis is a physiological process of tissue vascularization involving the growth of new blood vessels into a tissue wherever there is a need for them. For example, in a condition of oxygen deprivation as this might similarly be the case after wound formation, it is thought that cells release angiogenic factors thus inducing new vessel growth. For instance, vascular endothelial growth factor is perceived as the most important factor inducing proliferation of endothelial cells, the cells that form the vessels, leading to vascularization.

However, this physiological process might be deregulated in several pathological conditions, leading to an excessive and unnecessary or even harmful formation of new vessels, which is also referred to as neovascularization. On the one hand, this condition of neovascularization itself might cause a disease or pathological condition, e.g. in case of excessive scar formation or neovascular glaucoma. On the other hand, neovascularization promotes the progression of certain diseases as this is e.g. triggered by several solid solid tumors, e.g. breast cancer, prostate cancer or lymphomas like Hodgkin or non-Hodgkin lymphomas, or non-solid tumors like multiple myeloma.

Since angiogenesis or neovascularization is a hallmark of tumors, it is a concept in anti-cancer therapy to inhibit the formation of new vessels and thus to "starve" the tumor. Several new compounds have been developed aiming at blocking the proliferation and migration of endothelial cells. For instance, a monoclonal antibody against VEGF—bevacizumab (Avastin)—is successfully used in patients with various tumors to prevent metastasis and to shrink the tumors.

In addition to antibodies blocking VEGF and its receptor VEGFR small molecules are widely used as tyrosine-kinase-inhibitors (TKIs like Sunitinib and $2^{nd}$ generation drugs Dovitinib=TKi 258) are summarized in reviews by Mukherji et al. or Heidegger et al. in the context of prostate cancer (Mukherji D, Temraz S, Wehbe D, Shamseddine A: Angiogenesis and anti-angiogenic therapy in prostate cancer. Critical Reviews in Oncology/Hematology 87 (2013) 122-131; Heidegger I, Massoner P, Eder I E, Pircher A, Pichler R, Aigner F, Bektic J, Horninger W, Klocker H: Novel therapeutic approaches for the treatment of castration-resistant prostate cancer. Journal of Steroid Biochemistry & Molecular Biology 138 (2013) 248-256).

However, the intake of bevacizumab or small molecule inhibitors may be accompanied with several serious and/or less serious side effects; moreover, development of drug resistance is regularly observed in the clinical setting during the course of the treatment. Hence, there is a need for novel target molecules for anti-angiogenic therapy, the therapy being associated with less side effects.

Recently, steroid hormones have been controversially evaluated for their effect on angiogenesis. For instance, Frank-Lissbrant and colleagues described the rapid neovascularization in rat ventral prostate lobe of castrated rats after repeated subcutaneous dosing of testosterone. (Franck-Lissbrant I, Häggström S, Damber J E, Bergh A: Testosterone stimulates angiogenesis and vascular regrowth in the ventral prostate in castrated adult rats. Endocrinology 1998; 139(2): 451-6).

Further, Liao et al. described an effect of testosterone to promote vascular endothelial cell migration of cultured human umbilical endothelial cells (HUVECs) (Liao W, Huang W, Guo Y, Xin M, Fu X: Testosterone promotes vascular endothelial cell migration via upregulation of ROCK-2/moesin cascade. Mol Biol Rep (2013) 40:6729-6735).

A role of testosterone in regulating endothelial function and playing a role in the development and maturation of endothelial progenitor cells in the context of erectile physiology is further suggested in a review of Traish and Galoosian (Traish A M, Galoosian A: Androgens modulate endothelial function and endothelial progenitor cells in erectile physiology. Korean J Urol 2013; 54:721-731).

Eisermann et al. reported that the androgen analog R1881 induces VEGF expression in prostate cancer cell lines, thereby probably leading to VEGF-induced angiogenesis (Eisermann K, Broderick C J, Bazarov A, Moazam M M, Fraizer G C: Androgen up-regulates vascular endothelial growth factor expression in prostate cancer cells via an Sp1 binding site. Molecular Cancer 2013, 12:7).

In contrast to that, Chao et al. described anti-angiogenic effects of SR16388, a synthetic steroid with binding properties to the ER alpha and ER beta receptor, (Chao W R, Amin K, Shi Y, Hobbs P, Tanabe M, Tanga M, Jong L, Collins N, Peters R, Laderoute K, Dinh D, Yean D, Hou C, Sato B, Alt C, Sambucetti L.: SR16388: a steroidal antiangiogenic agent with potent inhibitory effect on tumor growth in vivo. Angiogenesis. 2011 March; 14(1):1-16).

The unpredictable effects on angiogenesis are seen also with other well known androgens, which are meanwhile either all banned from the market or withdrawn due to their side effects. Thomas et al. described that Danazol (17α-Ethinyl-17β-hydroxyandrost-4-eno [2,3-d]isoxazol) inhibits certain endothelial cell functions such as proliferation and tube formation but lacks the inhibition of the critical step of invasion into tissue (Thomas G W, Rael L T, Shimonkevitz R, Curtis C G, Bar-Or R, Bar-Or D: Effects of danazol on endothelial cell function and angiogenesis. Fertil Steril. 2007 October; 88 (4 Suppl):1065-70). Due to its androgenic properties (virilization, increase of free testosterone despite inhibition of testosterone synthesis) and its unfavorable profile it was withdrawn from market.

Nandrolone, 17β-Hydroxyestr-4-en-3-on, also a well-known anabolic drug, exerts certain anti-proliferative properties on HUVEC cells (D'Ascenzo S, Millimaggi D, Di Massimo C, SaccaniJotti G, Botrè F, Carta G, Tozzi-Ciancarelli M G, Pavan A, Dolo V.: Detrimental effects of anabolic steroids on human endothelial cells. Toxicol Lett. 2007 Mar. 8; 169 (2):129-36.) However, it is unknown, whether this translates in inhibition of angiogenesis since in an animal model of amyotrophic lateral sclerosis it was observed that nandrolone increases formation of TGF-beta, which is known to stimulate the expression of one of the most potent angiogenic factors, i.e. VEGF (Galbiati M, Onesto E, Zito A, Crippa V, Rusmini P, Mariotti R, Bentivoglio M, Bendotti C, Poletti A. The anabolic/androgenic steroid nandrolone exacerbates gene expression modifications induced by mutant SOD1 in muscles of mouse models of amyotrophic lateral sclerosis. Pharmacol Res. 2012 February; 65(2):221-30). In contrary, Nandrolone reduced VEGF levels in muscles of exercising rats (Paschoal M, de Cassia Marqueti R, Perez S, Selistre-de-Araujo H S. Nandrolone inhibits VEGF mRNA in rat muscle. Int J Sports Med. 2009 November; 30(11):775-8).

Stanazolol (17α-Methyl-5α-androstano[3,2-c]pyrazol-17β-ol) increases the expresssion of TGF beta 1, which is known to increase the production of the most potent angiogenic factor VEGF (Cao Y, Townsend C M, Ko T: Transforming growth factor-beta (TGF-beta) induces vascular endothelial growth factor (VEGF) and plasminogen activator inhibitor-1 (PAI-1) gene expression through Smad3 transcription factor. ACS, 2005 Volume 201, Issue 3, Suppl. 17-18).

Moreover, Thorpe et al. showed that heparin adipic hydrazide- (HAH-) linked cortisol might represent novel angiogenesis inhibitors for the treatment of cancer and other angiogenic diseases (Thorpe P E, Derbyshire E J, Andrade S P, Press N, Knowles P P, King S, Watson G J, Yang Y C, Rao-Bette M.: Heparin-steroid conjugates: new angiogenesis inhibitors with anti-tumor activity in mice. Cancer Res. 1993 Jul. 1; 53(13):3000-7.)

In the light of the various potential target molecules of steroid hormones, e.g. steroid hormone receptors or enzymes, it becomes evident that the outcome of an interaction of a defined cell or tissue with defined steroids is different from gender to gender, from tissue to tissue and the specific pattern of steroid receptors available and active. The specific biological response to steroid hormones is influenced by (i) differences in the expression pattern of e.g. steroid hormone receptors, (ii) the expression of enzymes and (iii) differences in the expression of receptor co-factors (co-activators or co-repressors) modulating the receptor response and (iv) the presence of steroids in the cell culture, organ or tissue. Prediction of a biological response towards a natural steroid or synthetic analogue appears difficult; based on the available literature the skilled person may even predict that testosterone like compounds may induce angiogenesis.

There is a need, and thus it is an objective of the present invention, to provide an effective angiogenesis inhibitor, that is able to inhibit endothelial and/or smooth muscle cell proliferation and/or migration and/or to reduce the synthesis or expression of VEGF and/or of VEGFR, thus inhibiting neovascularization in diseases involving excessive regenerative processes, i.e. processes which occur in various diseases.

These objectives as well as others, which will become apparent from the following description of the present invention, are attained by the subject-matter of the independent claims. Some of the preferred embodiments of the present invention are defined by the subject matter of the dependent claims.

SUMMARY OF THE INVENTION

Various aspects, advantageous features and preferred embodiments of the present invention as summarized in the following items, respectively alone or in combination, contribute to solving the object of the invention.

1. A compound defined by the formula 1

Formula 1 wherein
a, b and c respectively denote, independently from each other, a single bond or a double bond, with the proviso that at least one of a, b and c represents a double bond, and with the proviso that if a is single bond and b is double bond, $R_2$ is not H;
$R_1$ is either hydrogen or $C_1$ to $C_6$ alkyl;
$R_2$ is either $OR_5$ or hydrogen, wherein $R_5$ is hydrogen or $C_1$ to $C_{12}$ straight chain or branched alkyl;
$R_3$ is, in case of c being a single bond, either hydrogen or $C_1$ to $C_6$ alkyl, or in case of c being a double bond, $CHR_5$, wherein $R_5$ is the same as defined before;
$R_4$ is hydrogen, $C_1$ to $C_{12}$ alkyl, phenyl unsubstituted or substituted by $C_1$ to $C_{12}$ alkyl or $COR_6$ acyl group; $R_6$ being hydrogen, $C_1$ to $C_{12}$ straight chain or branched alkyl, phenyl or benzoyl, respectively, unsubstituted or substituted by $C_1$ to $C_{12}$ alkyl, or any group leading to hydroxyl upon biological metabolization or chemical deprotection, particularly an ester, ether, acetale, carbonate, carbamate, phosphate, phosphonate, ketal, sulfate, or sulfonate, and salts thereof,
for use in a medical treatment as angiogenesis inhibitor.

2. The compound defined by the formula 1

Formula 1 wherein
a, b and c respectively denote, independently from each other, a single bond or a double bond, with the proviso that at least one of a, b and c represents a double bond, and with the proviso that if a is single bond and b is double bond, $R_2$ is not H;

$R_1$ is either hydrogen or $C_1$ to $C_6$ alkyl;

$R_2$ is either $OR_5$ or hydrogen, wherein $R_5$ is hydrogen or $C_1$ to $C_{12}$ straight chain or branched alkyl;

$R_3$ is, in case of c being a single bond, either hydrogen or $C_1$ to $C_6$ alkyl, or in case of c being a double bond, $CHR_5$, wherein $R_5$ is the same as defined before;

$R_4$ is hydrogen, $C_1$ to $C_{12}$ alkyl, phenyl unsubstituted or substituted by $C_1$ to $C_{12}$ alkyl or $COR_6$ acyl group; $R_6$ being hydrogen, $C_1$ to $C_{12}$ straight chain or branched alkyl, phenyl or benzoyl, respectively, unsubstituted or substituted by $C_1$ to $C_{12}$ alkyl, or any group leading to hydroxyl upon biological metabolization or chemical deprotection, particularly an ester, ether, acetale, carbonate, carbamate, phosphate, phosphonate, ketal, sulfate, or sulfonate, and salts thereof, for use in the therapy of inflammation and/or cancer by inhibiting the proliferation or synthesis of, either alone or in combination: endothelial cell proliferation, smooth muscle cell proliferation, endothelial cell migration, smooth muscle cell proliferation, vascular endothelial growth factor (VEGF), vascular endothelial growth factor receptor (VEGFR), fibroblast growth factor receptor 13 (FGFR 13), platelet derived growth factor receptor (PDGFR) α and/or ß, and mast/stem cell growth factor receptor (SCFR; also known as c-Kit or tyrosine-protein kinase Kit or CD117).

3. The compound for use according to item 1 or 2, wherein the compound is defined by a and c being a single bond, b being a double bond, and $R_2$ being $OR_5$, $OR_5$ being as defined in claim 1, preferably wherein $R_5$ is either hydrogen or $C_1$ to $C_6$ straight chain or branched alkyl, and R4 is either hydrogen or $COR_6$ with $R_6$ being $C_1$ to $C_6$.

4. The compound for use according to any of items 1 to 3, wherein the compound is 4-hydroxytestosterone (4-OHT) or its salts or esters.

5. The compound for use according to any one of the preceding items for use as an inhibitor of neovascularization in a pathological condition involving regenerative processes.

6. The compound for use according to any one of the preceding items for preventing or inhibiting neovascularization in an inflammatory condition.

7. The compound for use according to item 6, wherein the inflammatory condition is selected from the group consisting of arthritis, inflammatory bowel diseases, eczema, neurodermatitis.

8. The compound for use according to any one of items 1 to 5 for preventing or inhibiting neovascularization triggered by a tumor.

9. The compound for use according to any of item 8, wherein neovascularization is triggered by a tumor of breast tissue, preferably breast cancer, or tumor of prostatic tissue, preferably prostate cancer.

10. The compound for use according to any one of the preceding items 1 to 5 in a prophylaxis or treatment of a solid tumor and metastasis thereof.

11. The compound for use according to item 10, wherein said solid tumor is selected from the group consisting of renal cancers such as kidney cell carcinoma, colorectal cancer, lung cancer, brain cancer and particularly glioblastoma, ovarian cancer, pancreatic cancer, and lymphoma, and metastasis thereof.

12. The compound for use according to any one of items 1 to 5 in a prophylaxis or treatment of a non-solid tumor and metastasis thereof.

13. The compound for use according to item 9, wherein said non-solid tumor is multiple myeloma and metastasis thereof.

14. The compound for use according to any one of items 1 to 5 for use in a prophylaxis or treatment of a vascular or vasoproliferative neoplasm, particularly an endothelial cell tumor selected from the group consisting of hemangiomas.

15. The compound for use according to any one of the preceding items 1 to 7 for preventing or treating an eye-related disease.

16. The compound for use according to any one of items 1 to 5 for use in a prophylaxis or treatment of an eye-related disease selected from the group consisting of diabetic retinopathy, macular degeneration, eye inflammation, particularly keratitis, corneal vascularization, vascular injection into the vitreous body, vascularization of the eye lens.

17. The compound for use according to any one of the items 1 to 5 for preventing or inhibiting neovascularization in wound repair including transformation of regular functional tissue into soft tissue.

18. The compound for use according to item 17 to reduce overshooting scar formation in organs such as the liver or heart after acute or chronic injury or on the skin.

19. The compound for use according to any one of the items 1 to 5 for preventing or inhibiting vascular malformations, in particular hemangioma in skin or solid organs (liver, brain, heart).

20. The compound for use according to any one of the items 1 to 5 for preventing or inhibiting cardiovascular diseases, particularly high blood pressure, stenosis or restenosis of blood vessels, and arteriosclerosis.

21. The compound for use according to any one of the items 1 to 5 for a treatment against obesity.

22. The compound for use according to any one of the items 1 to 5 for a treatment against endometriosis.

23. A pharmaceutical composition comprising a compound of the formula as defined in any of the preceding items and a pharmaceutically acceptable carrier and/or excipient for use in a medical treatment according to any of the preceding items.

24. The pharmaceutical composition according to item 23, wherein the pharmaceutical composition is prepared for dermal, mucosal or submucosal, transdermal, i.m., s.c., i.v., oral or suppository administration or instillation into cavities.

25. The pharmaceutical composition according to items 23 or 24, wherein the pharmaceutical composition is prepared for oral use, subcutaneous, cutaneous, intramuscular intravenous, intraocular, nasal or transdermal administration.

26. A combination comprising
   (i) an active substance selected from the group consisting of antibodies directed against VEGF, VEGFR or soluble VEGFR/VEGFR hybrids, and tyrosine kinase inhibitors, and
   (ii) a compound defined by the formula 1

Formula 1 wherein
a, b and c respectively denote, independently from each other, a single bond or a double bond, with the proviso that at least one of a, b and c represents a double bond, and with the proviso that if a is single bond and b is double bond, $R_2$ is not H;
$R_1$ is either hydrogen or $C_1$ to $C_6$ alkyl;
$R_2$ is either $OR_5$ or hydrogen, wherein $R_5$ is hydrogen or $C_1$ to $C_{12}$ straight chain or branched alkyl;
$R_3$ is, in case of c being a single bond, either hydrogen or $C_1$ to $C_6$ alkyl, or in case of c being a double bond, $CHR_5$, wherein $R_5$ is the same as defined before;
$R_4$ is hydrogen, $C_1$ to $C_{12}$ alkyl, phenyl unsubstituted or substituted by $C_1$ to $C_{12}$ alkyl or $COR_6$ acyl group; $R_6$ being hydrogen, C, to $C_{12}$ straight chain or branched alkyl, phenyl or benzoyl, respectively, unsubstituted or substituted by $C_1$ to $C_{12}$ alkyl, or any group leading to hydroxyl upon biological metabolization or chemical deprotection, particularly an ester, ether, acetale, carbonate, carbamate, phosphate, phosphonate, ketal, sulfate, or sulfonate, and salts thereof, preferably for use as defined in any one of the preceding items.

27. A pharmaceutical composition comprising a combination according to item 26.
28. Use of a compound or a pharmaceutical composition as defined in any of items 1 to 27 as an anti-angiogenic agent in a medical treatment.
29. Use of a combination according to item 26 or 27 as an anti-angiogenic agent in a medical treatment.

DESCRIPTION OF THE DRAWINGS

FIGS. 1 A and B: Proliferation assay upon exposure of HUVEC cells to 4-OHT and TKI 258 using WST-1 tests, resp. alone or in combination.

DETAILED DESCRIPTION OF THE INVENTION

The present invention is now described in more detail by preferred embodiments and examples, which are however presented for illustrative purpose only and shall not be understood as limiting the scope of the present invention in any way.

The present invention provides a compound of the general formula 1 defined above, which has surprisingly been found to effectively inhibit angiogenesis, and particularly any one or a combination of (i) to (vi):
(i) inhibition of endothelial cell proliferation;
(ii) inhibition of smooth muscle cell proliferation;
(iii) inhibition of endothelial cell migration;
(iv) inhibition of smooth muscle cell migration;
(v) reduction of VEGF protein expression or synthesis;
(vi) reduction of VEGFR protein expression or synthesis;
(vii) reduction of protein expression or synthesis of functionally related growth factors, including that of fibroblast growth factor receptor 13 (FGFR 13), of platelet derived growth factor receptor (PDGFR) α and/or β, and of mast/stem cell growth factor receptor (SCFR; also known as c-Kit or tyrosine-protein kinase Kit or CD117).

Thus, it is particularly suitable for the treatment of diseases involving excessive regenerative processes including neovascularization in tissue. Further, any of the anti-cancer/anti-proliferative and/or anti-inflammatory treatments (i) to (vii) above will be specifically and selectively effective in patients affected by such abnormal proliferation, and/or in special tissue and organ targets in patients where such abnormal proliferation occur. The compound of formula 1 and the preferred embodiments thereof as specified above (i.e. the compound of 1 and preferably wherein a and c are a single bond, b is a double bond, and $R_2$ is $OR_5$, $OR_5$ being as defined above, preferably wherein $R_5$ is either hydrogen or $C_1$ to $C_6$ straight chain or branched alkyl and R4 is either hydrogen or $COR_6$ with $R_6$ being $C_1$ to Ce; more preferably wherein the compound is 4-hydroxytestosterone (4-OHT) or its salts or esters) has surprisingly found to exert anti-angiogenic activity and inhibitory effects specified as items (i) to (vii) above. With the proviso that if in the structure of formula 1, symbol a is single bond and b is double bond, $R_2$ is not H, it is ensured that no testosterone-related or testosterone-like effects are exerted.

Importantly, the abovementioned tissue can specifically be a tissue or organ in the human body, in which (neo) vascularization may take place and may be triggered by a particular tumor, such as cancerous or non-cancerous breast tissue, prostate tissue, any intestinal tissue, lung tissue, renal tissue, the brain, the eye, ovarian tissue or the vascular tissue per se in the context of vascular anomalies, being for example vascular or vasoproliferative neoplasms such as hemangiomas or vascular malformations such as slow-flow vascular malformations, capillary malformation, venous malformation, lymphatic malformation, fast-flow vascular malformations, arterial malformation, arteriovenous malformation, arteriovenous fistula or combined vascular malformations (various combination of the above).

Therefore, the compound of formula 1 is highly useful for pathological conditions or situations triggering (neo)vascularization, being for instance in respective cases of tumors or any inflammatory conditions. The compound of formula 1 is highly useful for prophylaxis or treatment of other cancers and/or a metastasis thereof, where anti-angiogenesis or vascularization/neovascularization or cases of aforementioned inhibition or reduction (i) to (vii) is relevant, for example for prophylaxis or treatment of renal cancer such as kidney cell carcinoma, colorectal cancer, lung cancer, brain cancer, particularly glioblastoma ovarian cancer, multiple myeloma, lymphoma, inflammatory diseases such as e.g. rheumatoid arthritis, wound repair to reduce scar formation (especially in organs such as the liver or heart after acute or chronic injury or on the skin), vascular malformations, vascular or vasoproliferative neoplasms, endothelial cell tumors, such as hemangiomas (especially in, liver, brain and/or heart), eye-related diseases such as (diabetic) retinopathy, macular degeneration, eye inflammation, cardiovascular diseases, particularly high blood pressure, stenosis or restenosis of blood vessels, for example caused by arteriosclerosis, particularly atherosclerosis, for example following an injury and/or in the context of angioplasty or stent implantation.

Furthermore, the angiogenesis inhibitor of the present invention can be used as anti-obesity agent, as it is known that blood vessels in adipose tissue never fully mature, and are thus destroyed by angiogenesis inhibitors (D. Bruemmer, Targeting Angiogenesis as Treatment for Obesity; Arteriosclerosis, Thrombosis, and Vascular Biology 32 (2), 161-162, 2012).

Moreover, the angiogenesis inhibitor of the present invention can be used as an active substance to treat endometriosis, due to a linkage between anti-angiogenesis and a positive effect against endometriosis.

Furthermore, the compound of formula 1 is highly useful in the treatment of tumors such as renal cell carcinomas, which are often developing resistance to the initial anti-cancer treatment, thus requiring a second line therapy using e.g. mTOR inhibitors or $2^{nd}$ generation TKIs. Hence, the compound of the present invention provides an alternative to the classical anti-cancer therapy after formation of resistance.

Moreover, the invention provides a combination comprising a compound of formula 1 or its preferred structural forms specified above, and an active substance selected from the group consisting of antibodies directed against VEGF, VEGFR or soluble VEGFR/VEGFR hybrids, and tyrosine kinase inhibitors (TKIs). "Combination" means a fixed combination within a common composition or common dosage form, or a separate but associated combination, e.g. by way of concomitantly or sequentially administered compositions, respectively containing the compound of formula 1 and the specified antibody or TKI. Preferred Examples of said antibodies include the monoclonal antibody against VEGF bevacizumab (Avastin), and preferred examples of TKIs include sunitinib, dovitinib (TKI 258), imatinib, sorafenib and those TKIs further reported by Mukherji et al. (2013) and Heidegger et al. (2013) cited above.

Furthermore, the compound of formula 1 is highly useful for treating angiogenesis triggered by a tumor, particularly a cancer or a metastasis thereof, for example breast cancer or prostate cancer or a metastasis thereof.

Surprisingly and distinct from prior investigations of related compounds to inhibition of hormone-related tumor cell growth and metastasis formation, in particular in relation to breast cancer or prostate cancer (WO 2007/131736, WO 2007/131737), it was found by the inventors that compounds of the general formula 1 as defined above inhibit the proliferation and/or migration of human endothelial cells and/or smooth muscle cells. Furthermore, it was surprisingly found that compounds of the general formula 1 as defined above reduce the expression of VEGF and VEGFR in an inflamed and/or cancerous environment. For instance in cases of anti-cancer treatments, and again independent and distinct from treatments involving inhibition of hormone-related tumor cell growth and metastasis formation as it was the case e.g. in relation to breast cancer or prostate cancer (WO 2007/131736, WO 2007/131737), the findings of the present invention allow to make use of anti-angiogenesis treatment in corresponding new clinical settings. For example, unlike a direct destruction of cancerous target cells and tissues, inhibition of angiogenesis according to the present invention allows to effectively inhibit further tumor growth and tumor vascularization through anti-angiogenesis and/or through inhibition or reduction effects (i) to (vii) specified above. In this way, the means by which tumors can nourish themselves and thus by which metastasis can be interrupted, which eventually will lead to tumor starvation and thereby indirect anti-tumor activity. For instance, treatments of such hormone-related cancers and metastasis, such as breast cancer or prostate cancer, can be effected with inhibition of angiogenesis triggered by such a tumor.

Further, distinct from mere general anabolic effects such as stabilization of collagen and optionally other supportive proteins and thereby considering stabilization of supportive tissue and related treatments like myocardial infarction and brain infarction, arteriosclerosis, urinary incontinence and the like (WO2009/062683), again the findings of the present invention allow to make use of anti-angiogenesis treatment in corresponding new clinical settings.

Generally with respect to therapeutic applications, new clinical settings are characterized by differences with respect to, for example, patient group, timing (e.g. decisions when and where to start treatment), dosage, and combination with other treatments.

Without being bound to any theory, this is assumed to be due to a down-regulation of e.g. VEGF and/or VEGFR and/or other proliferation-, cancer- and/or inflammation-relevant growth factors or growth factor receptors, e.g. in cells of the inflamed and/or cancerous tissue mentioned above, e.g. any epithelial cell forming the above-mentioned organ and/or the above-mentioned tumor or in stroma cells, thus indirectly having an anti-angiogenic effect on vascular cells, or due to a downregulation of VEGF and/or VEGFR and/or other proliferation-, cancer- and/or inflammation-relevant growth factors or growth factor receptors in endothelial and/or smooth muscle cells per se. Thus, the present invention provides a compound for the treatment of diseases involving an undesired proliferation and/or migration of endothelial and/or smooth muscle cells, for example for the diseases mentioned above.

Based on these surprising findings of the present invention, the compound of formula I credibly is useful in therapeutic clinical settings where functionally related growth factors are involved, notably fibroblast growth factor receptor 13 (FGFR 13), platelet derived growth factor receptor (PDGFR) α and/or ß, and mast/stem cell growth factor receptor (SCFR; also known as c-Kit or tyrosine-protein kinase Kit or CD117).

This inhibitory effect can be exploited in various aspects:
1. neovascularization triggered by a tumor can be effectively inhibited;
2. neovascularization into inflamed tissue can be inhibited;
3. abnormal proliferation of endothelial and/or smooth muscle cells perse can be inhibited, as this may be the pathological alteration in endothelial cell tumors or vascular malformations.

In use, the abovementioned compounds may be administered to the patient in an amount suitable for inhibiting the proliferation and/or migration of endothelial and/or smooth muscle cells. Further, the use may be determined by an appropriate application condition, such as type of patient, or type of target site or organ or pharmaceutical composition or formulation being able to transport the aforementioned activities in vivo to the designated final target site or organ within a patient.

Further, the abovementioned compound may be administered topically and/or application to mucosa, e.g. in the form of an ointment, a cream, a lotion, a gel, a spray, a powder, an oil or a transdermal plaster, also comprising depot usage forms (including pellets); it may be administered parenterally, e.g. intramuscularly, or by intravenous or subcutaneous injection or infusion, or intranasal, instillation into cavities (e.g. bladder, abdomen, intestine), and/or orally, e.g., in the form of tablets, capsules, sugar or film coated tablets, liquid solutions or suspensions or rectally, e.g. in the form of suppositories, or intraocularly, e.g. in form of injection and as eye drops.

The applied amount for inhibiting the proliferation and/or migration of endothelial and/or smooth muscle cells can be suitably chosen for example depending on the age, weight, conditions of the user and administration form; for example the dosage adopted for oral administration to adult humans may range from about 1 to about 150-1000 mg per application, from 1 to 5 times daily.

Accordingly, said compounds may be comprised in pharmaceutical compositions further comprising a pharmaceutically acceptable carrier and/or excipient and/or diluent.

For topical use, the composition may be formulated by including, for example, vegetable oils and fats such as almond oil, peanut oil, olive oil, peach kernel oil, castor oil; plant extracts; ethereal oils; furthermore vegetable waxes and synthetic and animal oils; fats and waxes such as stearic acid and stearate esters, lauric acid and lauric esters, sorbitane esters, ceteryl alcohols; lecithin, lanolin alcohols, carotene, fragrances, mono- or polyhydric alcohols, urea, surfactants such as poloxamers, Tweens, and the like; preservatives and colorants etc. Formulation as an oil-in-water or water-in-oil emulsion is preferred.

Solid oral forms may for example contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols, poloxamers, tocopheryl polyethylene glycol succinate (TPGS); binding agents, e.g. starches, arabic gums, gelatine, methylcellulose, carboxymethylcellulose or polyvinyl pyrrolidone; disaggregating agents, e.g. a starch, alginic acid, alginates or sodium starch glycolate; effervescing mixtures; dyestuffs, sweeteners; wetting agents, such as lecithin, polysorbates, laurylsulphates; and, in general, non-toxic and pharmacologically inactive substances used in pharmaceutical formulations. These preparations may be manufactured in known manner, for example, by means of mixing, granulating, tabletting, sugar-coating, or film-coating processes. The liquid dispersions for oral use may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol, poloxamers, or TPGS.

The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

The solutions for intravenous or subcutaneous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The active compound content of a suitable composition may be at least 0.0001 wt %, for example between 0.0001 and 20% by weight, preferably 0.6% until 10% by weight, further preferably 1 and 5% by weight, of the compound used according to the invention.

If substances are admixed to promote skin penetration, their content, when using hyaluronidases, can be, for example, between 0.01 and 1% by weight, preferably 0.05 and 0.2% by weight, when using dimethylisosorbide or DMSO between 1 and 25% by weight, preferably 5 and 10% by weight, poloxamers 0.5-30%, TPGS 0.5-30% The present invention is further illustrated by the description of the following examples, which are however only for illustrative purposes and shall not be understood in any limiting manner.
Preparation and Treatment of Human Umbilical Vein Endothelial Cells All of the experiments described in the following chapters were performed at least in triplicates, mostly using 2 different cell numbers and various incubation times. All experiments were additionally run in several replicates (one HUVEC in different passages as well as different preparations.

Briefly, human umbilical vein endothelial cells (in the following HUVEC) were freshly isolated out of human umbilical cords by methods known in the art and were used in the experiments from passage p4 up to passage p10 to prevent any artefacts originating from in vitro changes of the cells.

In all experiments, the C-19 steroid compound 4-OHT was added to the cells in the indicated concentration in EGM-2 medium (Lonza) in order to avoid any artefacts originating from exogenous factors contained in the medium. All experiments were performed at least three times and showed the same pattern of response.

Identity, differentiation and long term-stability of gene expression of cultivated HUVEC-cells was assessed by using immunocytochemical staining with anti-von Willebrand Factor (vWF) antibody. Expression of vWF is highly specific for endothelial cells. Stability of vWF expression was quantified between passage 1 and 10. Within this time schedule only minor changes occur within the cultivation period and between the different batches used.

Example 1: Inhibition of Endothelial Cell Proliferation

As one method to determine cell proliferation of mammalian endothelial cells, proliferation assays were performed as described below.

For determining the proliferation rates, WST-1 tests were performed. Essentially, 1000 HUVEC cells/well were seeded in a 96-well plate and exposed to the indicated concentrations of 4-OHT (also denoted by lab code CR 1447) for 5 days. Inhibition of proliferation was quantified by measuring the enzymatic cleavage of the tetrazolium salt WST-1 to formazan by cellular mitochondrial dehydrogenases as a readout for cell viability, wherein cell viability of treated cells is expressed as the percentage (%) of untreated controls containing only the solvent in appropriate concentrations. Means of 3 independent experiments performed in triplicates are shown in FIG. 1A.

Figure 1A:
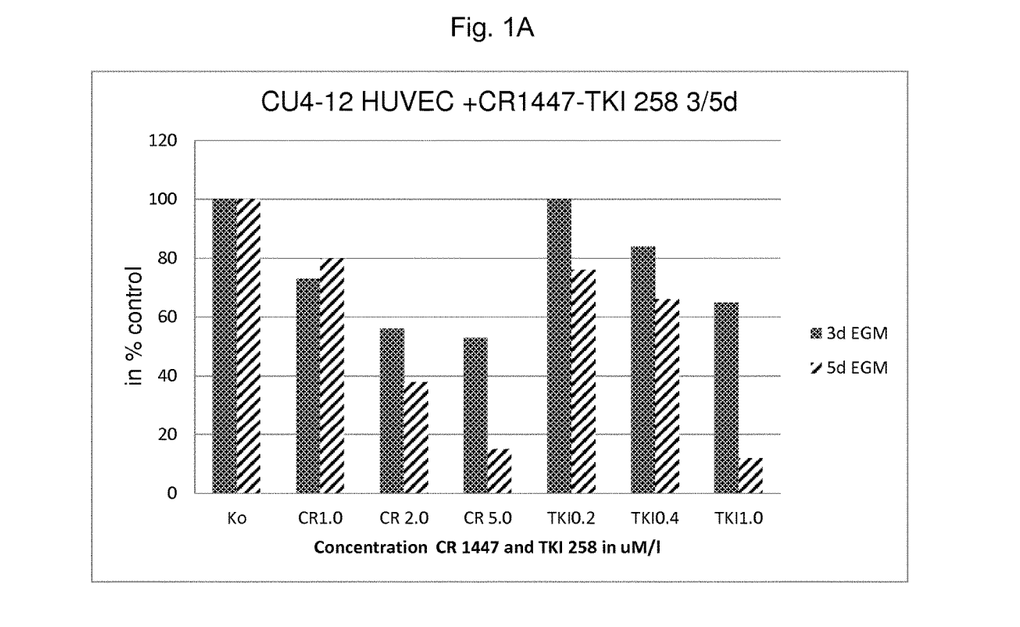
Figure 1B:
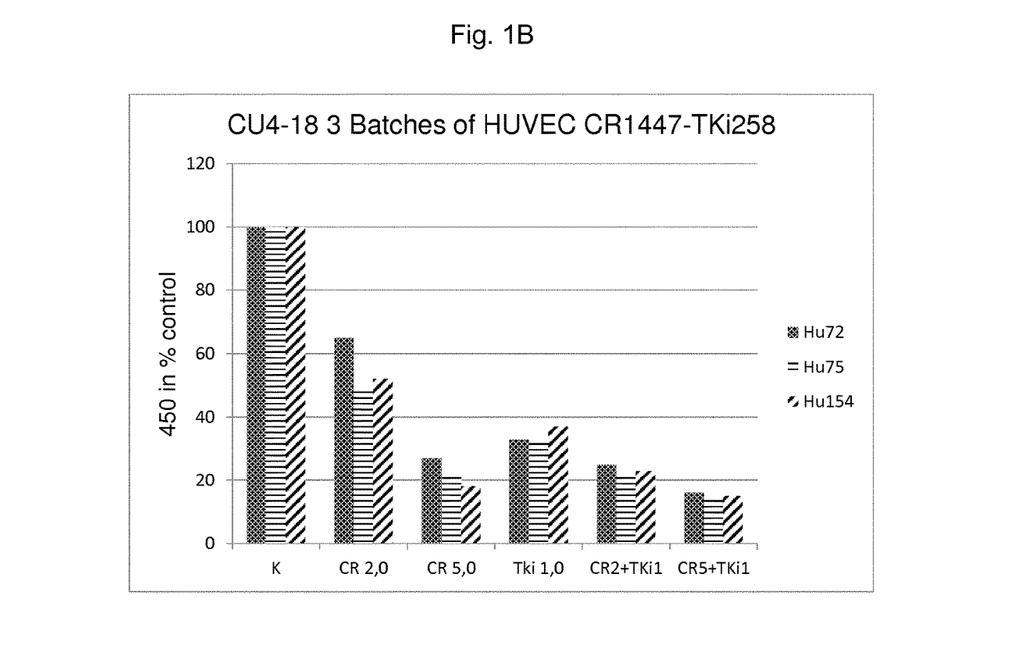

As shown in FIG. 1A, growth inhibition by 4-hydroxytestosterone at all concentrations of 1, 2 and 5 µM was shown to be highly significant (p<0.001) in all 3 HUVEC cell cultures (t-test), comparable with the known VEGF inhibitor TKI258 (Dovitinib) (0.2, 0.4 and 1.0 µM). Cells were grown and subcultured in Endothelial Cell Growth medium (EGM)

for 3 and 5 days, respectively. As further shown in FIG. 1B, growth inhibition of CR 1447 in combination with TKI 258 (compared with each compound alone) is also highly significant (p<0.001) in all 3 HUVEC cell cultures (t-test).

Figure 2A:
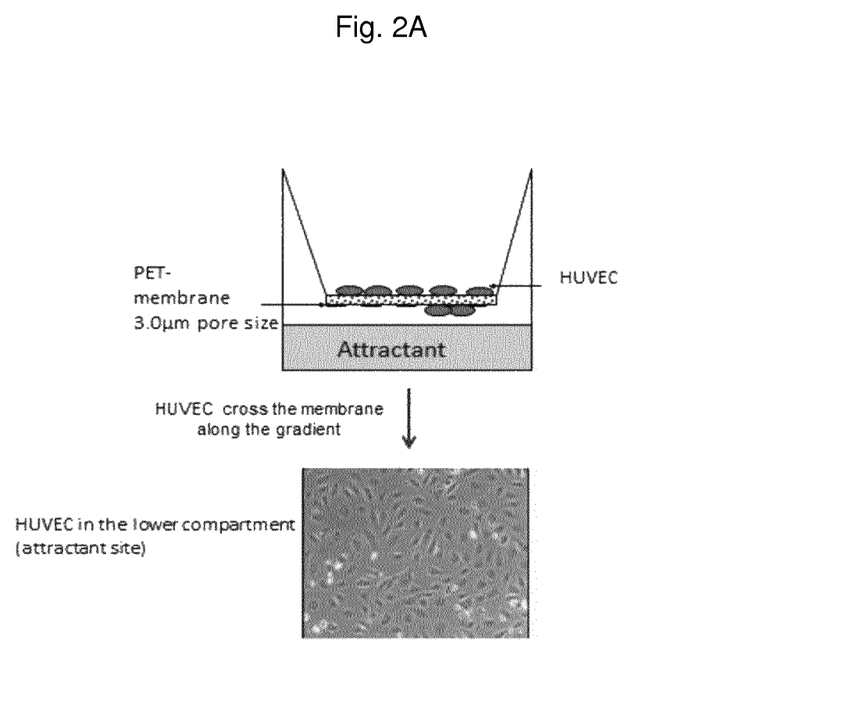
FIG. 2A Principle of transwell migration assay.

Example 2: Inhibition of Endothelial Cell Migration Using Transwell Migration Assay A prerequisite of angiogenesis is the capability of endothelial cells to migrate into the tissue. This process is observed in wound healing and also in the process of tumor growth. Endothelial cells migrate into the tissue along a gradient of factors such as VEGF. This behavior can be studied in an in vitro model of migration using a transwell system, as e.g. apparent from FIG. 2A. Specifically, FIG. 2A shows the typical arrangement of a transwell assay to monitor cell migration.

For studying the migration of HUVEC cells using the transwell system with PET-membranes having a 3 μm pore size (24-wells w/o fibronectin-coating), HUVEC cells in different cell numbers were placed in the upper compartment, whereas the attractant was placed in the lower compartment. The number of cells on the attractant site of the membrane was compared with the number of cells visible in a control system (buffer control) and with the attractant (VEGF) in the presence of 4-OHT.

Figure 2B:
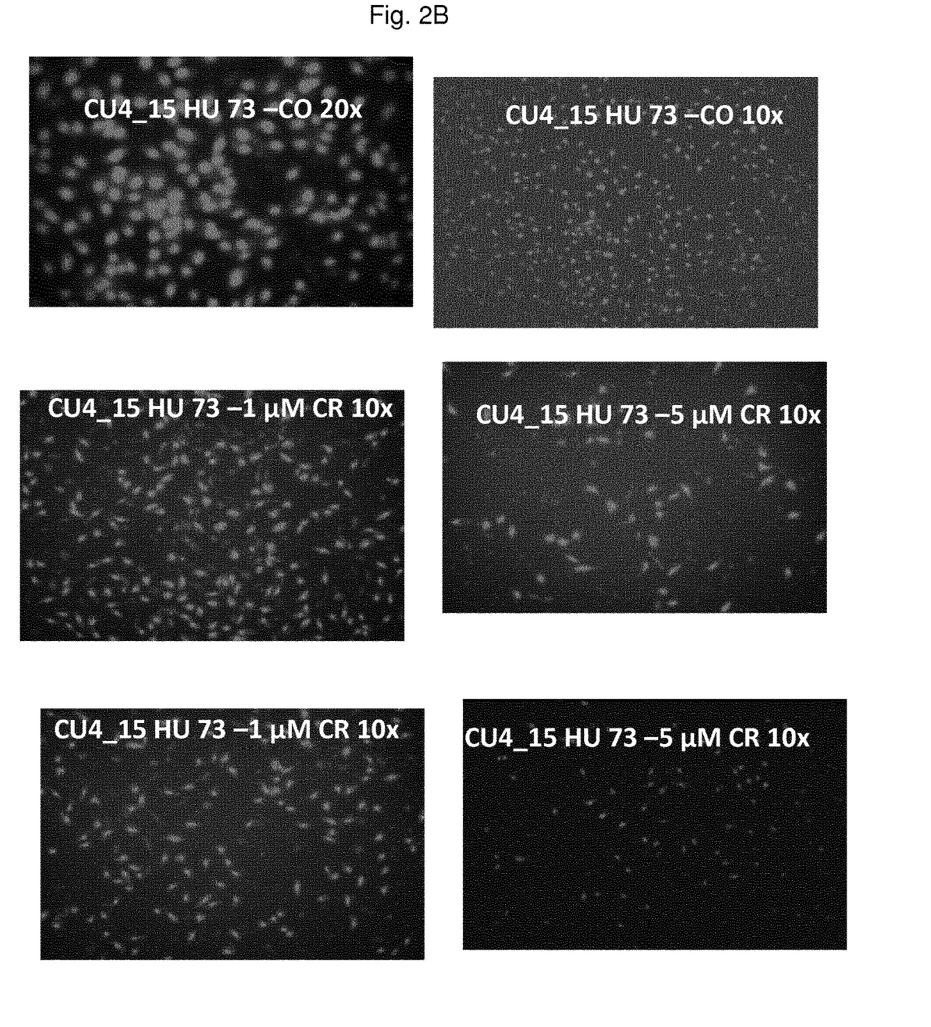
FIG. 2B Analysis of transwell migration assay upon exposure of HUVEC cells to 4-OHT.

FIG. 2B shows a typical image of three independent experiments, specifically by a transwell-assay using FI-block membranes and propidium-iodide staining of migrated HUVECs. Cells were seeded as described and migration was performed for 48 hrs using VEGF as attractant in the lower chamber. The figures represent examples from 3 independent experiments. Compared to control (Co). As can be seen, 4-OHT significantly inhibits the migration of cells into the membrane, indicated by the remarkably reduced number of migrating cells in the samples subjected to treatment by 4.OHT (code "CR").

Example 3: Inhibition of Endothelial Cell Migration Using Wound Healing Assay Another method for studying cell migration is the wound healing (scratch) assay. This assay resembles the events occurring in an acute wound healing process. By release of factors from the wound area endothelial cells migrate into the scratch area, which shall resemble the process of healing and closure of the wound by vascularization and later scar formation.

In summary, HUVEC cells were seeded in a 12-well plate and allow to grow until reaching confluency. Subsequently, a scratch was set, thereby removing the cells within the scratch area. The cells were exposed to 10 μM of 4-OHT and the migration of endothelial cells into the scratch area was monitored microscopically using a schedule from 2 up to 48 hrs, depending on the individual experimental design.

Figure 3:
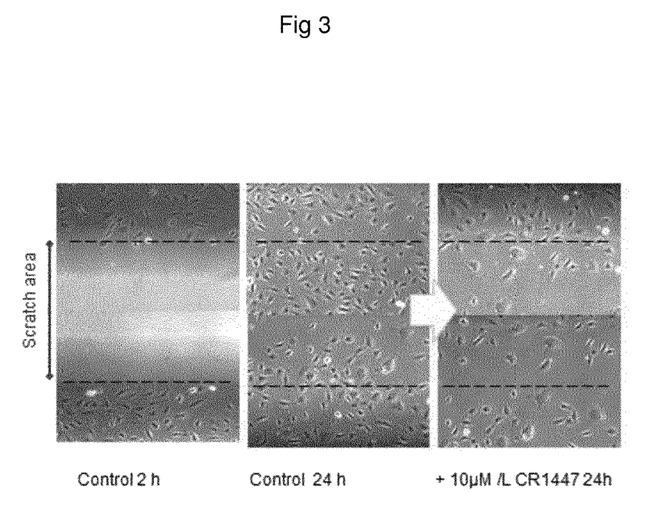
FIG. 3 Wound healing assay of HUVEC cells upon exposure to 4-OHT.

A typical image out of three independent experiments is shown in FIG. 3 representing typical results from 10 independent experiments using different concentrations and time schedules. As shown, endothelial cell migration is effectively inhibited by 4-OHT as demonstrated in the wound-healing assay (scratch assay). After 24 h a clear reduction of migration of HUVEC cells into the scratch area as compared to the untreated control cells is seen under the influence of 4-OHT (CR 1447).

Example 4: Tube Migration Assay

After migration into the tissue of a scratch, HUVEC cells change their growth characteristics and form microvessels. This effect can be assessed microscopically.

HUVEC cells were seeded on matrigel (7 mg/ml). Cell suspensions as well as gels containing 10 μM/L 4-OHT were added upon seeding, It was allowed to form branching points during adherence onto this surface mimicking basal membrane character. Tube formation was analyzed microscopically after 12 and 48 hours.

Figure 4:
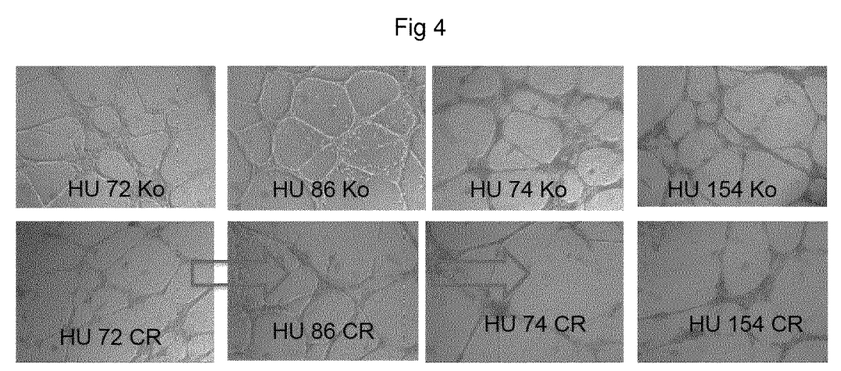
FIG. 4 Tube migration assay of HUVEC cells upon exposure to 4-OHT using matrigel.

A typical image out of three independent experiments is shown in FIG. 4. Accordingly, tube formation of human endothelial cells (HUVEC) is significantly inhibited by the application of 4-OHT ("CR"-specified samples in the lower row). When the human endothelial cells were subjected onto matrigel pads, branching points as one marker of tube formation are inhibited by 4-OHT as compared to untreated controls (red arrows). Thus, 4-OHT markedly inhibited branching of the cells and massively disturbed the linear cell-cell-connections on the gel, indicating remarkable (neo) vascularization inhibition.

The invention claimed is:

1. A method of treating or preventing a pathological condition involving angiogenesis in a patient, the method comprising:
    administering an effective amount of a compound to the patient, wherein the compound is defined by Formula 1:

Formula 1 wherein:
a, b and c respectively denote, independently from each other, a single bond or a double bond, with the proviso that at least one of a, b and c represents a double bond, and with the proviso that if a is single bond and b is double bond, $R_2$ is not H;
$R_1$ is either hydrogen or $C_1$ to $C_6$ alkyl;
$R_2$ is either $OR_5$ or hydrogen, wherein $R_5$ is hydrogen or $C_1$ to $C_{12}$ straight chain or branched alkyl;
$R_3$ is, in case of c being a single bond, either hydrogen or $C_1$ to $C_6$ alkyl, or in case of c being a double bond, $CHR_5$, wherein $R_5$ is the same as defined before; and
$R_4$ is hydrogen, $C_1$ to $C_{12}$ alkyl, phenyl unsubstituted or substituted by $C_1$ to $C_{12}$ alkyl or $COR_6$ acyl group; $R_6$ being hydrogen, $C_1$ to $C_{12}$ straight chain or branched alkyl, phenyl or benzoyl, respectively unsubstituted or substituted by $C_1$ to $C_{12}$ alkyl, or any group leading to hydroxyl upon biological metabolization or chemical deprotection, the group being an ester, ether, acetale, carbonate, ca late, phosphate, phosphonate, ketal, sulfate, or sulfonate; and salts thereof.

2. A method of treating a patient suffering from inflammation comprising:
    administering an effective amount of a compound to the patient, thereby inhibiting the proliferation or synthesis of, either alone or in combination: endothelial cell proliferation, smooth muscle cell proliferation, endothelial cell migration, smooth muscle cell proliferation, vascular endothelial growth factor, vascular endothelial growth factor receptor, fibroblast growth factor receptor 13, platelet derived growth factor receptor α and/or ß, and mast/stem cell growth factor receptor, wherein the compound is defined by Formula 1:

Formula 1 wherein a, b and c respectively denote, independently from each other, a single bond or a double bond, with the proviso that at least one of a, b and c represents a double bond, and with the proviso that if a is single bond and b is double bond, $R_2$ is not H;

$R_1$ is either hydrogen or $C_1$ to $C_6$ alkyl;

$R_2$ is either $OR_5$ or hydrogen, wherein $R_5$ is hydrogen or $C_1$ to $C_{12}$ straight chain or branched alkyl;

$R_3$ is, in case of c being a single bond, either hydrogen or $C_1$ to $C_6$ alkyl, or in case of c being a double bond, $CHR_5$, wherein $R_5$ is the same as defined before;

$R_4$ is hydrogen, $C_1$ to $C_{12}$ alkyl, phenyl unsubstituted or substituted by $C_1$ to $C_{12}$ alkyl or $COR_6$ acyl group; $R_6$ being hydrogen, $C_1$ to $C_{12}$ straight chain or branched alkyl, phenyl or benzoyl, respectively, unsubstituted or substituted by $C_1$ to $C_{12}$ alkyl, or any group leading to hydroxyl upon biological metabolization or chemical deprotection, the group being an ester, ether, acetale, carbonate, carbamate, phosphate, phosphonate, ketal, sulfate, or sulfonate, and salts thereof.

3. The method according to claim 1, wherein the compound is defined by a and c being a single bond, b being a double bond, and $R_2$ being $OR_5$.

4. A method of inhibiting neovascularization in a pathological condition, comprising:

administering an effective amount of a compound to the patient, wherein the compound is defined by Formula 1:

Formula 1 wherein:

a, b and c respectively denote, independently from each other, a single bond or a double bond, with the proviso that at least one of a, b and c represents a double bond, and with the proviso that if a is single bond and b is double bond, $R_2$ is not H;

$R_1$ is either hydrogen or $C_1$ to $C_6$ alkyl;

$R_2$ is either $OR_5$ or hydrogen, wherein $R_5$ is hydrogen or $C_1$ to $C_{12}$ straight chain or branched alkyl;

$R_3$ is, in case of c being a single bond, either hydrogen or $C_1$ to $C_6$ alkyl, or in case of c being a double bond, $CHR_5$, wherein $R_5$ is the same as defined before; and $R_4$ is hydrogen, $C_1$ to $C_{12}$ alkyl, phenyl unsubstituted or substituted by $C_1$ to $C_{12}$ alkyl or $COR_6$ acyl group; $R_6$ being hydrogen, $C_1$ to $C_{12}$ straight chain or branched alkyl, phenyl or benzoyl, respectively unsubstituted or substituted by $C_1$ to $C_{12}$ alkyl, or any group leading to hydroxyl upon biological metabolization or chemical deprotection, the group being an ester, ether, acetale, carbonate, carbamate, phosphate, phosphonate, ketal, sulfate, or sulfonate; and salts thereof.

5. The method according to claim 1, wherein the pathological condition is selected from the group consisting of arthritis, inflammatory bowel diseases, eczema, and neurodermatitis.

6. The method according to claim 1, where the pathological condition is vascularization triggered by breast cancer or by prostate cancer.

7. The method according to claim 1, wherein the pathological condition involving angiogenesis is associated with a solid tumor caused by a cancer selected from the group consisting of renal cancer, colorectal cancer, lung cancer, brain cancer, ovarian cancer, pancreatic cancer and lymphoma, and metastasis thereof.

8. The method according to claim 1, wherein the pathological condition is selected from the group consisting of:

hemangioma, eye-related diseases selected from the group consisting of retinopathy, macular degeneration, eye inflammation, corneal vascularization, vascular injection into the vitreous body, and vascularization of the eye lens, wound repair, or for transformation of regular functional tissue into soft tissue, to reduce overshooting scar formation, vascular malformations, in particular against hemangioma in skin or solid organs, hypertension, stenosis or restenosis of blood vessels, arteriosclerosis obesity, and endometriosis.

9. A method of treating a patient suffering from a pathological condition involving angiogenesis according to claim 1, wherein the step of administering the effective amount of the compound to the patient includes administering a pharmaceutically acceptable carrier and/or excipient.

10. A combination comprising:

(i) an active substance selected from the group consisting of antibodies directed against VEGF, VEGFR or soluble VEGFR/VEGFR hybrids, and oncogenic tyrosine kinase inhibitors, and (ii) a compound defined by the Formula 1:

Formula 1 wherein
- a, b and c respectively denote, independently from each other, a single bond or a double bond, with the proviso that at least one of a, b and c represents a double bond, and with the proviso that if a is single bond and b is double bond, $R_2$ is not H;
- $R_1$ is either hydrogen or $C_1$ to $C_6$ alkyl;
- $R_2$ is either $OR_5$ or hydrogen, wherein $R_5$ is hydrogen or $C_1$ to $C_{12}$ straight chain or branched alkyl;
- $R_3$ is, in case of c being a single bond, either hydrogen or $C_1$ to $C_6$ alkyl, or in case of c being a double bond, $CHR_5$, wherein $R_5$ is the same as defined before;
- $R_4$ is hydrogen, $C_1$ to $C_{12}$ alkyl, phenyl unsubstituted or substituted by $C_1$ to $C_{12}$ alkyl or $COR_6$ acyl group; $R_6$ being hydrogen, $C_1$ to $C_{12}$ straight chain or branched alkyl, phenyl or benzoyl, respectively, unsubstituted or substituted by $C_1$ to $C_{12}$ alkyl, or any group leading to hydroxyl upon biological metabolization or chemical deprotection, the group being an ester, ether, acetale, carbonate, carbamate, phosphate, phosphonate, ketal, sulfate, or sulfonate, and salts thereof.

11. The method according to claim 1, wherein $R_5$ is hydrogen or $C_1$ to $C_6$ straight chain or branched alkyl, and $R_4$ is hydrogen or $COR_6$ with $R_6$ being $C_1$ to $C_6$.

12. The method according to claim 1, wherein the compound is 4-hydroxytestosterone or its salts or esters.

13. The method according to claim 1, wherein the pathological condition is a non-solid tumor selected from the group consisting of multiple myeloma or metastasis thereof.

* * * * *

UNITED STATES PATENT AND TRADEMARK OFFICE
CERTIFICATE OF CORRECTION

PATENT NO. : 10,426,785 B2  
APPLICATION NO. : 15/535461  
DATED : October 1, 2019  
INVENTOR(S) : Gerhard Unteregger Page 1 of 1

It is certified that error appears in the above-identified patent and that said Letters Patent is hereby corrected as shown below:

On the Title Page

Item (72) Inventor: should read as:
Inventor: Gerhard Unteregger, Homburg/Saar (DE)

Signed and Sealed this
Third Day of December, 2019

Andrei Iancu
*Director of the United States Patent and Trademark Office*